(12) United States Patent
Turner, III

(10) Patent No.: US 6,250,304 B1
(45) Date of Patent: Jun. 26, 2001

(54) INTERNAL ALLOTROPY IMPLEMENT SEXUAL AID UTENSIL

(75) Inventor: Jacob Turner, III, 11115 Sherman, Los Angeles, CA (US) 90001

(73) Assignee: Jacob Turner, III, Sun Valley, CA (US)

( * ) Notice: Subject to any disclaimer, the term of this patent is extended or adjusted under 35 U.S.C. 154(b) by 0 days.

(21) Appl. No.: 09/442,300

(22) Filed: Nov. 19, 1999

Related U.S. Application Data

(60) Provisional application No. 60/121,245, filed on Feb. 23, 1999.

(51) Int. Cl.[7] ........................................... A61F 5/37
(52) U.S. Cl. ............................. 128/883; 128/884
(58) Field of Search ..................... 128/830–841, 128/883, 884

(56) References Cited

U.S. PATENT DOCUMENTS

| | | | |
|---|---|---|---|
| 5,353,811 | * 10/1994 | Davis | 128/884 |
| 5,769,090 | * 6/1998 | Brown | 128/884 |

* cited by examiner

Primary Examiner—Michael A. Brown
(74) Attorney, Agent, or Firm—Jacob Turner, III

(57) ABSTRACT

The invention is made of a soft but firm FDA approved polymer/thermoplastic medical grade containing within its structure different hardness and shape of material base cover support, resilient hollow receptacle tip, sharp pointed projectile, elongated solid circular implant with side port thru holes and a string. It can be lubricated in the manner of a condom. The resilient hollow receptacle tip, can be filled with a spermicide for a source of protection against any pre-ejaulation of semen in the act of attempting to penetrate the vagina. It is inserted into the vagina of the woman wearing it in the same way as a tampon lengthwise and pushing it into the vaginal cavity. Upon placement in the vagina, the invention blocks the entrance to the vagina, and exposes a resilient hollow receptacle tip covering a sharp projectile, which will inflict a sharp non-lethal pain to head of the penis attempting to penetrate the vagina. The invention is stabilized inside the vagina with the help of an elongated solid circular implant with side port thru holes and a string. This attaches to the base cover support. A woman can pinch grip the resilient hollow receptacle tip to remove the invention. It is re-useable. It can be worn for a few hours or overnight. It should not be worn for a straight 24 hours. A Physician can be consulted as to the proper insertion, and care of the invention. It can be made in different sizes to accommodate the various different female anatomy's. It can be worn by women of all ages

10 Claims, 4 Drawing Sheets

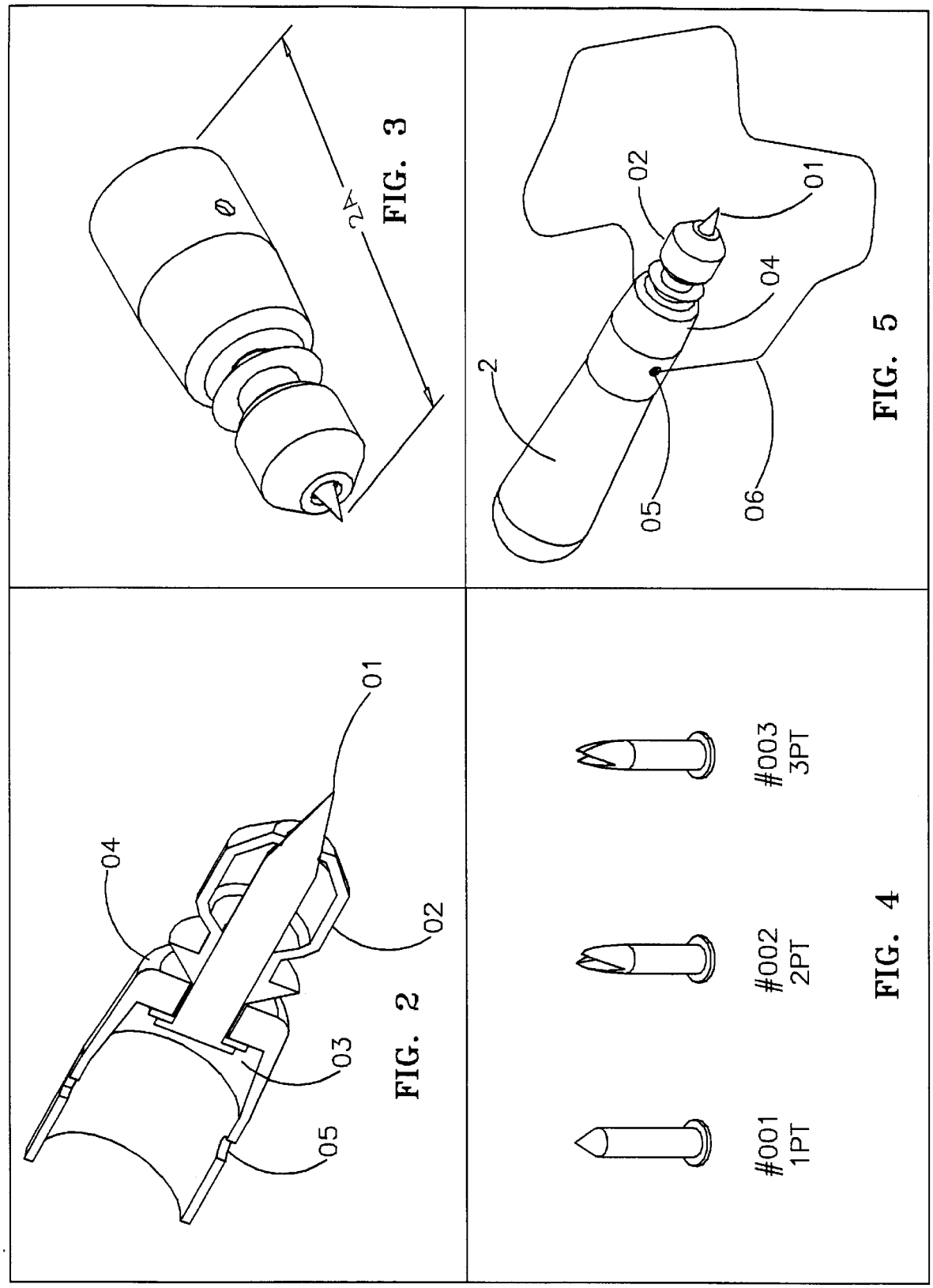

INTERNAL ALLOTROPY IMPLEMENT SEXUAL AID UTENSIL

This application claims benefit to provisional application No. 60/121,245 filed Feb. 23, 1999.

BRIEF SUMMARY

This type of invention is one that causes a non-lethal severe sharp pain to the head of the male penis and creates a blockage device inserted into the female vagina. The invention is made to prevent unwanted penal penetration, and to give a non-lethal pain if forced vagina penetration is attempted. It is an intra-vaginal anti-rape invention which is made of a medically approved FDA polymer thermoplastic material. It's structure consist of a resilient hollow tip, which covers a sharp pointed projectile ,and holds a contraceptive solution, which is attached to a base cover support which has two side port holes for the string from the elongated implant which secures the invention together and fills the vaginal cavity. The elongated implant can be substituted for a tampon depending upon the female using the invention. The purpose of the invention is to create a vaginal blocker internally with a sharp pointed projectile covered by a resilient hollow tip which will inflict a sharp severe non-lethal pain to the head of a male's penis if forced penetration is attempted. This invention is made to be worn by women of all ages. Size adjustments can be made according to each individual women wearing this invention. Men considering rape, after this invention becomes known, will hopefully not attempt it, with the dread that any women could be wearing this invention.

BRIEF DESCRIPTION OF THE DRAWINGS

FIG. 2. shows side view of invention internal implement allotrophy sexual aid utensil without the elongated implant shows sharp pointed projectile, resilient hollow tip, base cover support, two side port holes, the area where elongated implant or tampon attaches to invention.

FIG. 3. shows side view of internal implement allotrophy sexual aid utensil without elongated implant or tampon.

FIG. 4. shows the side view of three different shaped sharp pointed projectiles 01,002,003.

FIG. 5. shows side view of complete assembled invention with elongated implant attached, sharp pointed projectile, resilient hollow tip, base cover support ,two side port holes, elongated implant, attaching string from elongated implant.

DETAIL DESCRIPTION

Figure 1:
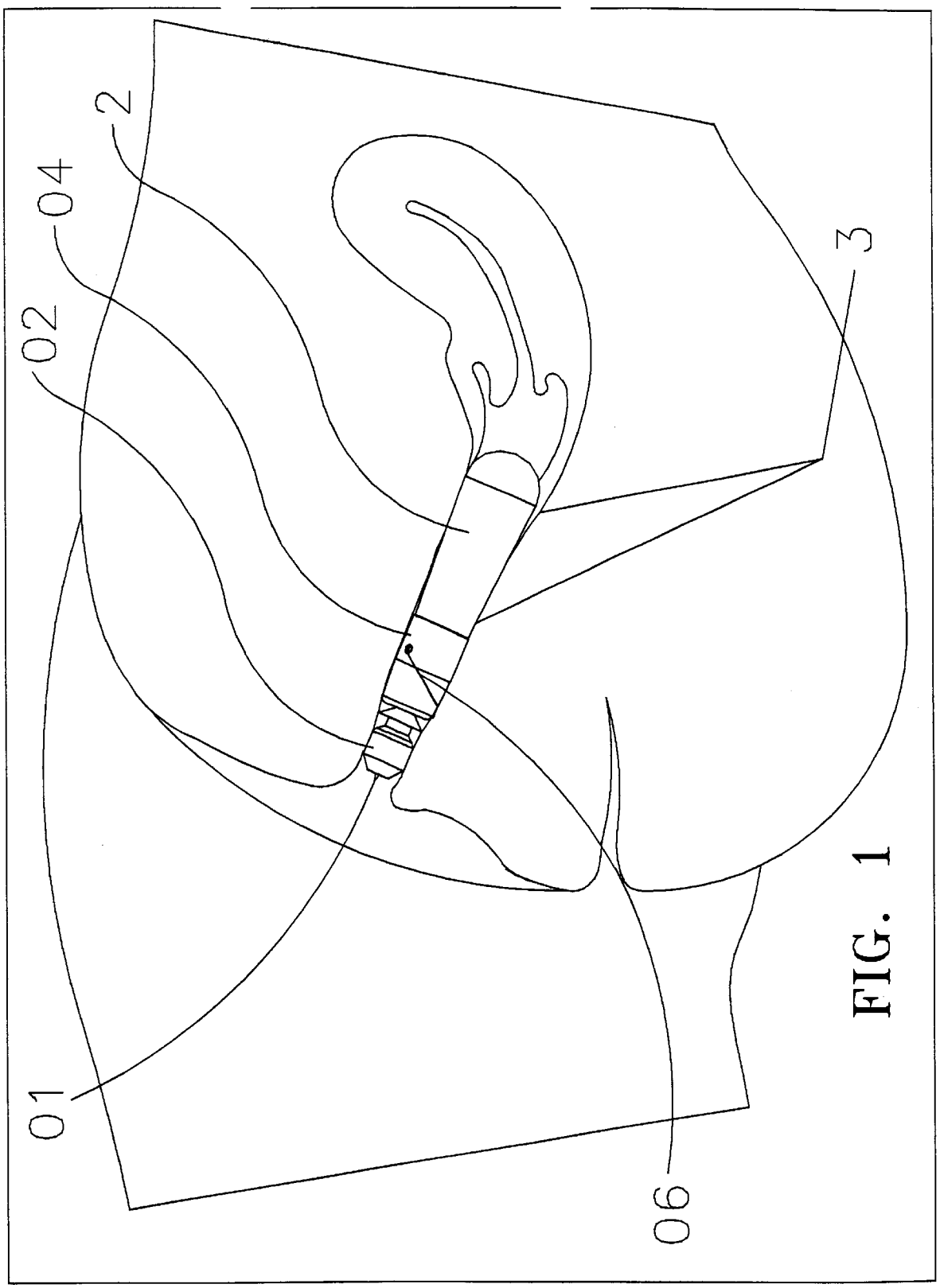
FIG. 1. shows a side view of the woman's anatomy wearing the invention inside the vaginal cavity with the sharp pointed projectile inside the resilient hollow tip attached to the base cover support and the elongated implant tied with a string which secure the invention inside the vaginal cavity facing the entrance of the vagina.
Figure 6:
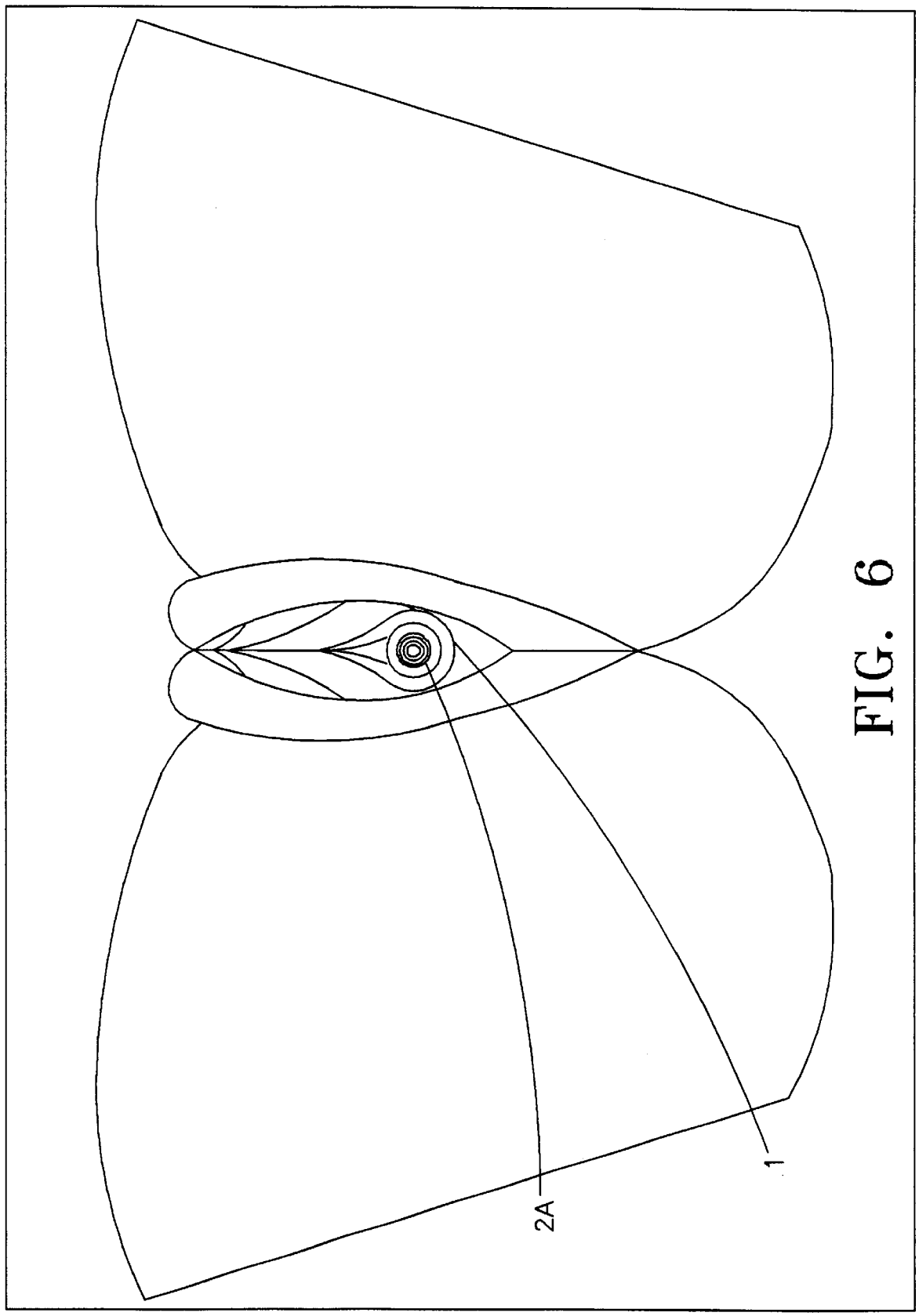
FIG. 6. shows rear view of woman's anatomy with invention inserted in vagina blocking the entrance of the vagina.
Figure 8:
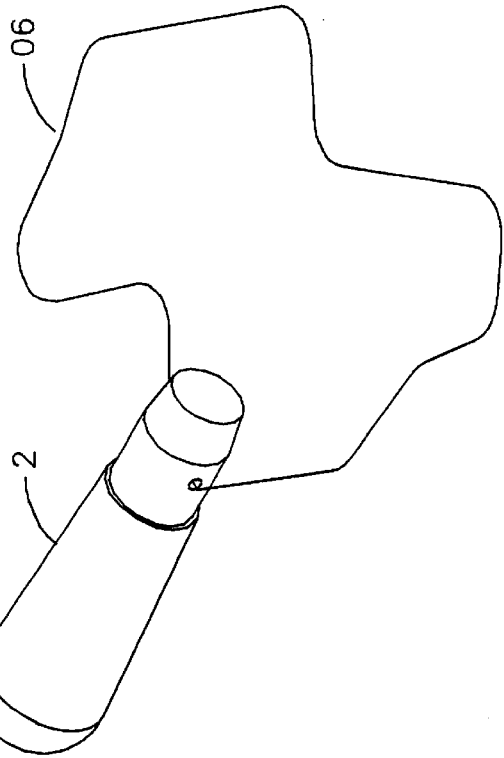
FIG. 8. shows side view of elongated implant with string.
Figure 7:
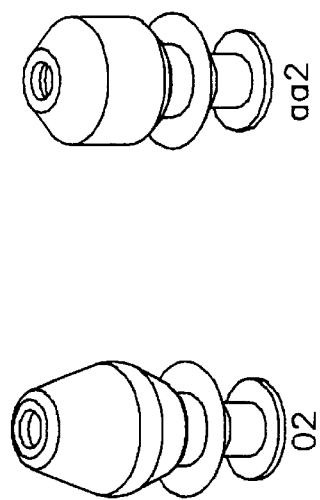
FIG. 7. shows side view of two different resilient hollow tips 02,aa2.
Figure 9:
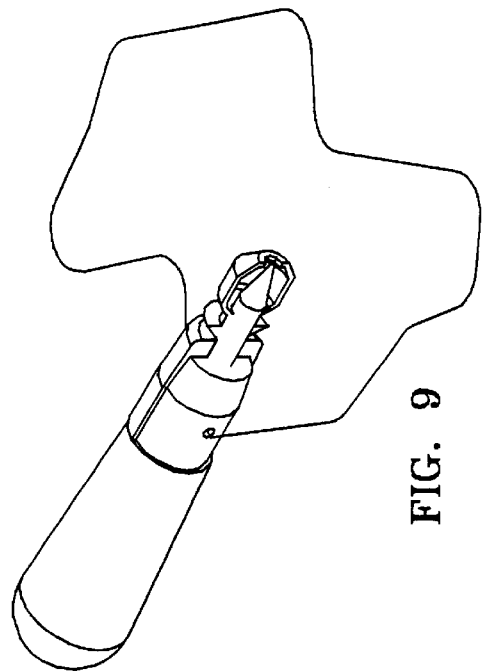
FIG. 9. shows side view of four interlocking parts of assembled invention with the elongated implant attached with string.

The subject matter which we refer to as the invention . . . Internal Implement Allotrophy Sexual Aid Utensil is four separate parts that interlock forming one device which is an open and circular elongated and interlocking device made of a medically FDA approved polymer thermoplastic, which is a soft and firm material. The invention is inserted into a females vagina. FIG. 1. Shows the side view of the woman's anatomy wearing the invention inside the vaginal cavity with the sharp pointed projectile 01, inside the resilient hollow tip 02, attached to the base cover support 04, and the elongated implant 2, tied with a string 06, which secures the invention inside the vaginal cavity 3, facing the entrance of the vagina. FIG. 2. shows the side view of the invention structure which include the base cover support 04, two side port holes 05, one sharp pointed projectile 01, and a resilient hollow tip 02. FIG. 3. shows the side view of the invention without the elongated implant 2, attached. FIG. 4. shows the side view of three different sharp pointed projectiles 01,002, 003. FIG. 5. shows side view of complete assembled invention with enlongated implanted 2, attached with string 06. FIG. 6. shows the rear view of the entrance of the vagina with the invention inserted. FIG. 7. shows the two different resilient hollow tips 02,aa2. FIG. 8. shows the elongated implant 2, with string 06. FIG. 9. Shows side view of the complete assembly of invention with its four attaching interlocking parts. If penetration is forced the resilient tip 02, recoils exposing the sharp pointed projectile 01, which will puncture the penis with a non-lethal sharp pain. This invention is re-useable, and can be made in different sizes. This invention is made to be worn by woman of all ages.

What is claimed is:

1. An intra-vaginal anti-rape device comprising a circular pointed projectile, a resilient hollow tip surrounding said circular pointed projectile, a base cover having an opening that said circular projectile and resilient hollow tip extend outwardly from.

2. The intra-vaginal device of claim 1, wherein said circular pointed projectile has different configurations.

3. The intra-vaginal device of claim 1, having a string attached to said base cover support.

4. The intra-vaginal device of claim 3, wherein the string extends through an opening in said base cover.

5. The intra-vaginal device of claim 1, wherein said circular projectile has sharp edges for delivering a non-lethal pain to a penis.

6. The intra-vaginal device of claim 1, wherein said resilient tip has different configurations.

7. The intra-vaginal device of claim 1, wherein said base cover has a contraceptive solution located therein.

8. The intra-vaginal device of claim 1, wherein said circular projectile is made of a hard material.

9. The intra-vaginal device of claim 1, wherein the device is made of polymer.

10. The intra-vaginal device of claim 9, wherein said polymer is a thermoplastic.

* * * * *